United States Patent [19]

Saint-Amour

[11] Patent Number: 4,520,672
[45] Date of Patent: Jun. 4, 1985

[54] THICKNESS MEASURING

[76] Inventor: John D. Saint-Amour, 158 E. Main St., Westboro, Mass. 01581

[21] Appl. No.: 409,589

[22] Filed: Aug. 19, 1982

[51] Int. Cl.³ .......................................... G01N 29/00
[52] U.S. Cl. ..................................... 73/622; 73/637; 264/40.1; 425/141
[58] Field of Search ............... 73/622, 637, 638, 640, 73/641, 644; 264/40.1, 40.3, 40.7; 425/135, 141, 149, 150

[56] References Cited

U.S. PATENT DOCUMENTS

| | | | |
|---|---|---|---|
| 3,183,709 | 5/1965 | Rankin et al. | 73/622 |
| 3,901,071 | 8/1975 | Hansen | 73/615 |
| 3,955,425 | 5/1976 | Corneau | 73/622 |
| 4,099,418 | 7/1978 | Bennett et al. | 73/622 |
| 4,152,380 | 5/1979 | Graves et al. | 264/40.7 |
| 4,328,708 | 5/1982 | Bagwell | 73/622 |
| 4,377,540 | 3/1983 | Cluett et al. | 264/40.3 |

FOREIGN PATENT DOCUMENTS

| | | | |
|---|---|---|---|
| 1164456 | 9/1969 | United Kingdom | 73/622 |
| 1370946 | 10/1974 | United Kingdom | 73/622 |

*Primary Examiner*—Stephen A. Kreitman
*Attorney, Agent, or Firm*—Charles Hieken

[57] ABSTRACT

Four ultrasonic probes in space quadrature are located near the input end of a water tank to define an opening for receiving extruded plastic tubing provided from an adjacent extrusion die. The probes are formed with passages that expel bubble-free water between the probes and tubing. Ultrasonic thickness measuring circuitry provides a wall thickness signal to a control signal source that also receives a diameter signal provided by a diameter sensor near the output end of the tank representative of the tube thickness. Compressed air is introduced inside the tubing through a pressure regulating valve that receives a pressure control signal from the control signal source, and the control signal source also provides speed control signals to a feed screw drive motor that drives the feed screw feeding plastic material into the extrusion die or the takeup reel drive motor that drives the takeup reel or other device receiving the finished tubing so as to maintain the diameter and wall thickness of the tubing substantially uniform.

11 Claims, 4 Drawing Figures

THICKNESS MEASURING

The present invention relates in general to thickness measuring and more particularly concerns novel apparatus and techniques for ultrasonically measuring the wall thickness of a thin tube as it is being extruded and developing control signals for maintaining the extruded tube within prescribed relatively tight tolerances.

Ultrasonic thickness gauges for measuring wall thicknesses are known. U.S. Pat. No. 3,901,071 describes a system with four ultrasonic probes positioned in space quadrature about the circumference of a pipe to monitor the pipe thickness by measuring the time interval between echoes from the outer and inner surfaces of the pipe. A multiplexing system operates the probes sequentially to provide four thickness signals provided by the respective probes. A signal averaging circuit averages these signals to provide a signal indicative of the average pipe thickness which may be used in a control loop to maintain constant average pipe thickness in a pipe extrusion system.

The present invention is concerned with measuring thickness of relatively thin-walled tubing used for medical applications, typically having a wall thickness of 0.029" and an inside diameter of the order of 0.1 inches. A system incorporating the invention has maintained wall thickness within +/−0.005" on a typical 0.019" wall, and inside diameter within +/−0.001" on a typical 0.100" tubing bore.

It is an important object of this invention to provide an improved ultrasonic thickness measuring system suitable for use in a thin-walled tube extrusion system so as to maintain thickness and diameter to relatively tight tolerances.

According to the invention, there are a plurality of probes circumferentially spaced about the tube being measured so as to focus energy on the inside wall of the tube with the probe, and separated from it by fluid, such as water, that is maintained bubble-free. A feature of the invention resides in positioning the probes as close to the extrusion die as practical so that the material is above a temperature where attenuation of acoustical energy is relatively high.

In a preferred system according to the invention, the ultrasonic probes are located in a water tank at the entrance end near the extrusion die for determining wall thickness with ultrasonic thickness measuring circuitry averaging the thickness signals derived from the four probes to provide an average thickness signal to a control signal source. An optical, laser, or other diameter sensor located outside the output end of the tank, and preferably after a dryer, measures the dry thickness signal of the tubing to provide an outside tube thickness to the control signal source. The control signal source may then provide control signals to a take-up reel drive motor that operates the take-up reel on which the finished tubing is wound, or to the feed screw drive motor that operates the feed screw that delivers hot plastic material for extrusion to the extrusion die and the pressure regulating valve that controls air pressure inside the extruded tube to thereby control tube wall thickness and diameter.

Numerous other features, objects and advantages of the invention will become apparent from the following specification when read in connection with the accompanying drawing in which.

Figure 1:
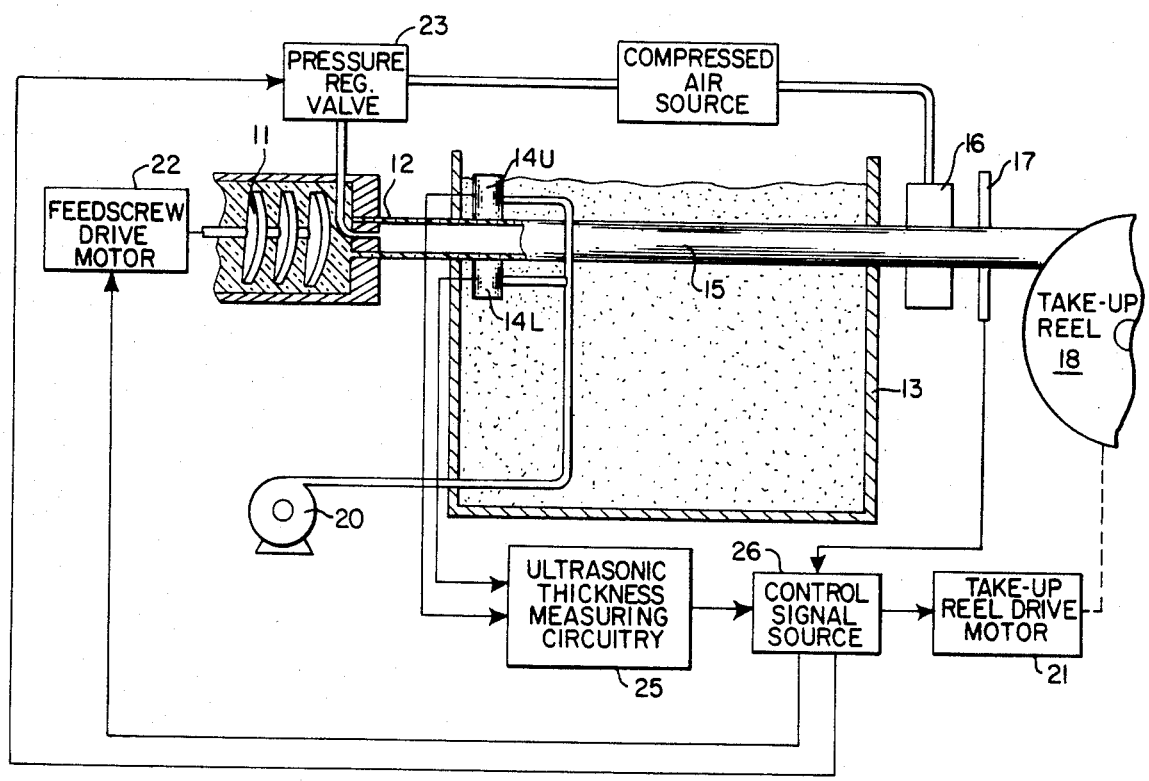
FIG. 1 is a combined diagrammatic-block diagram illustrating the logical arrangement of a system according to the invention.

With reference now to the drawing and more particularly FIG. 1 thereof, there is shown a combined diagrammatic-block diagram illustrating the logical arrangement of a system incorporating the invention for controlling wall thickness of thin flexible tubing. A feed screw 11 advances hot plastic material into extrusion die 12 that enters water tank 13 between four ultrasonic probes in space quadrature, two of which, 14U and 14L are shown in FIG. 1 near the input end of tank 13. The probes 14 are typically 8–10 inches from extrusion die 12 in a water tank about 30 feet long with tube 15 moving through at about 500/feetminute. The flexible tube 15 exits at the output end and passes through output air dryer 16, optical gauge 17 and then upon takeup reel 18. Takeup reel drive motor 21 drives takeup reel 18 or take-up rollers. Feed screw drive motor 22 drives feed screw 11. A compressed air source 23 delivers compressed air to dryer 16 and through pressure regulating valve 24 applies pressure to the inside wall of tubing 15. A pump or other means 20 forces water through openings in the probes to keep bubbles from developing between each probe and the tube wall. Bubbles would form if the probes were in static water. And water directly from a high pressure source carries dissolved gases that will escape from solution and form bubbles. Therefore, pump 20 receives water from a debubbled source, such as chilled water from the plant, and delivers the debubbled water to the probes at a rate typically 1–1.5 gallons per minute. Ultrasonic thickness measuring circuitry 25 processes the signals from each of the four probes to provide a signal representative of the average thickness of the wall.

The prior art approach avoided measuring ultrasonically near the extrusion die because it was thought that hot material attenuates ultrasonic energy too much. However, it has been discovered that if the measurement is made when the material is very hot very close to the extrusion die, the attenuation is actually lower than at a lower temperature above the temperature of the cold material. That is to say, it has been discovered that above a predetermined temperature where attenuation apparently is a maximum, attenuation actually reduces, thereby making it practical to measure ultrasonically near the extrusion die and thereby provide information that facilitates promptly making corrections in wall thickness to maintain an exceptionally high degree of uniformity while allowing a significant increase in production rate.

Locating the probes near the die takes advantage of the plastic wall tubing temperature being most stable there because temperature controllers maintain the plastic at a closely controlled temperature when passing through the extrusion die. Temperature stability contributes to wall measurement accuracy because the speed of sound through plastic varies with temperature, and variations in temperature thus affect measurement accuracy.

Diameter sensor 17 provides a signal to control signal source 26. Control signal source 26 responds to the tube outer diameter sensed by optical sensor 17 and the average thickness signal provided by ultrasonic thickness measuring circuitry 25 to provide control signals to takeup reel drive motor 21 or feed screw drive motor 22 and pressure regulator valve 23 for controlling thickness and outer diameter.

Varying the speed of feed, takeup or air pressure affects both tubing diameter and wall thickness. It has been discovered that it is preferred to make small changes in air pressure to hold diameter to tight tolerances and make speed changes to control wall thickness.

Figure 2:
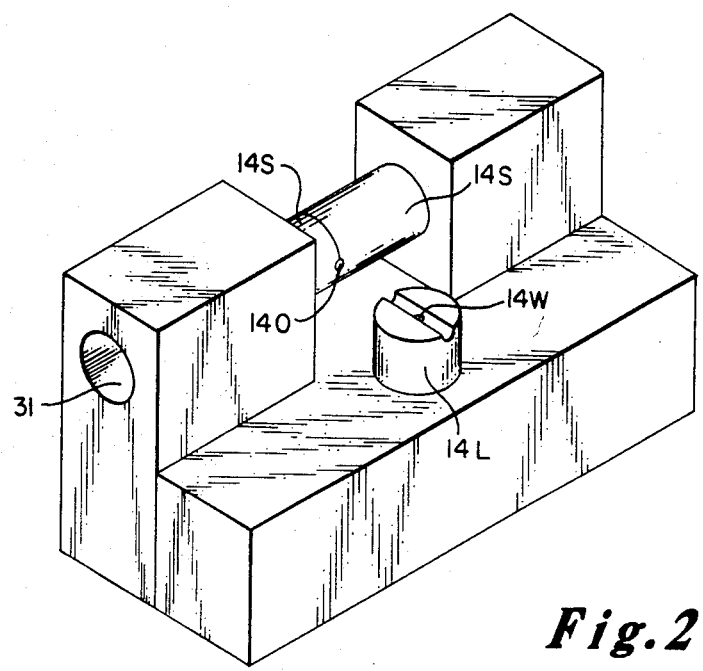
FIG. 2 is a perspective view illustrating the arrangement of ultrasonic probes.

Referring to FIG. 2, there is shown a perspective view of a preferred arrangement for supporting the ultrasonic probes with probe 14U omitted so as to better illustrate the structural arrangement, it being understood that probe 14U mates with probe 14L as side probes 14S are in mating engagement to form a generally rhombic channel 140 through which the extruded tubing passes. Note the opening 14W in lower probe 14L through which water and signals pass from the opening. Forcing a stream of water between the transducers and the tubing helps prevent air bubbles from developing and insures accurate measurements.

A preferred form of pressure regulator valve 23 is an air bubbler in which the air pressure may be regulated by controlling the height of water in the bubbler.

The specific form of control signal source 26 is not a part of the invention. A microprocessor may be employed that coacts with a keyboard for receiving prescribed limits on thickness and diameter.

Figure 3:
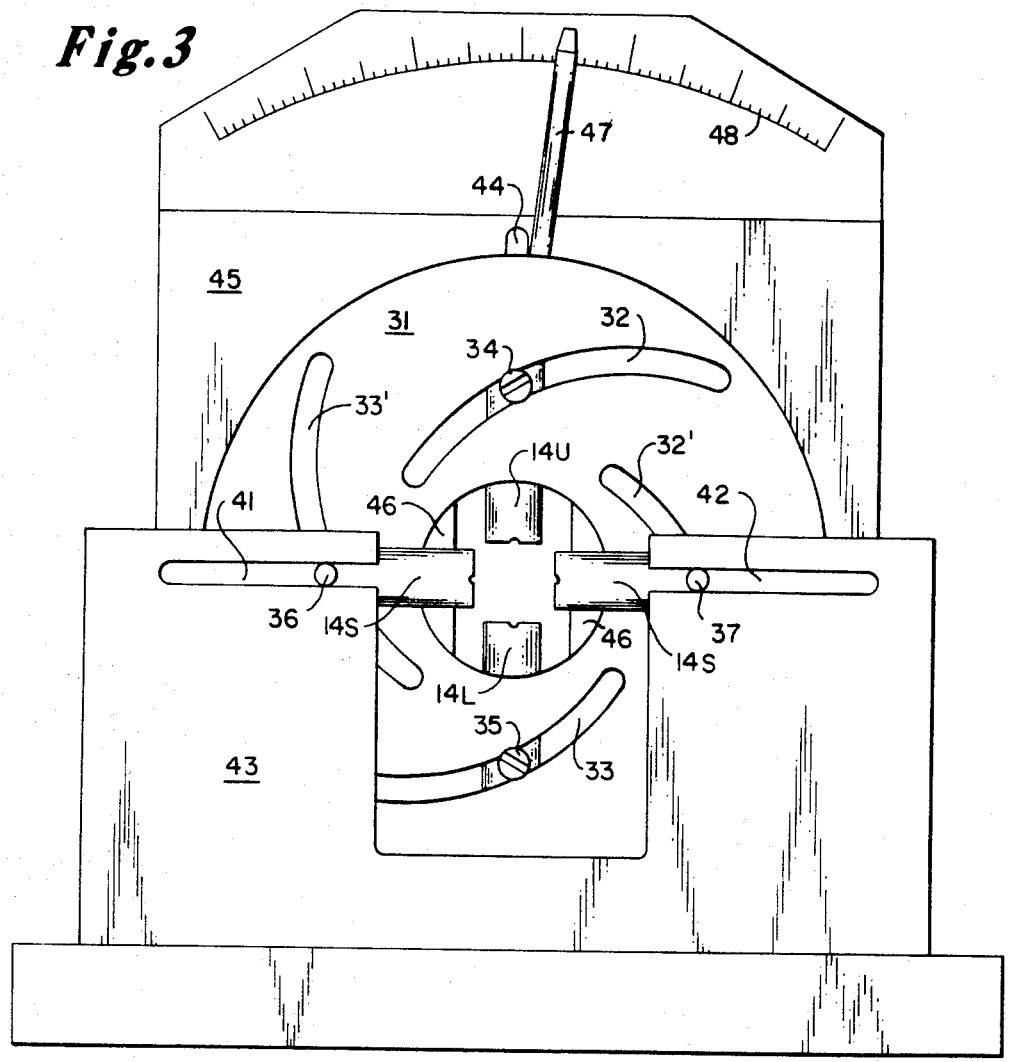
FIG. 3 is a pictorial representation of a slotted cam mount for the probes.

Referring to FIG. 3, there is shown a perspective view of a preferred form of probe support assembly looking toward the exit side of the probe assembly in an iris mount whereby rotating cam 31 simultaneously and equally radially displaces probes 14U, 14L and 14S. Slotted cam 31 is formed with four arcuate slots in space quadrature, such as 32, 32', 33 and 33', each progressively closer to the cam axis as a function of counterclockwise angular position. Each slot accommodates a captive shoulder screw, two of which are visible in FIG. 3, such as shoulder screws 34 and 35 in slots 32 and 33, respectively. Each shoulder screw is attached to a respective probe, shoulder screws 34 and 35 being attached to upper and lower probes 14U and 14L, respectively. A water fitting, such as 36 and 37, is seated in each probe opposite a respective shoulder screw and rides in a linear slot, such as side horizontal slots 41 and 42 in exit vertical support plate 43 and upper vertical slot 44 in entrance support plate 45. Cam plate 31 is annular and is supported in a cavity in blocks 43 and 45. A pointer 47 is attached to cam plate 31 to rotate therewith and indicate on scale 48 the tube dimensions, thereby facilitating positioning the probes for controlling the manufacture of tubes of different size.

Figure 4:
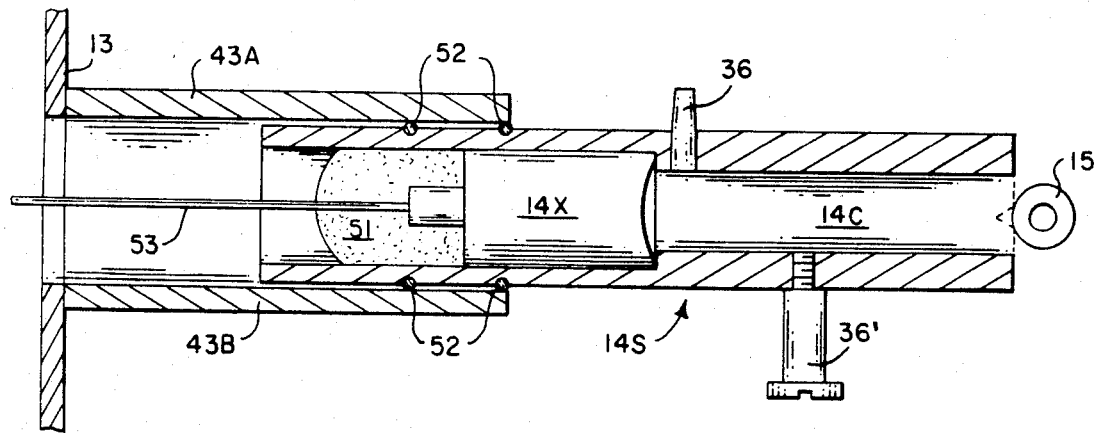
FIG. 4 is a pictorial representation, partly in section, illustrating how a transducer is telescopically supported.

Referring to FIG. 4, there is shown a pictorial representation, partially in section, illustrating how a transducer, such as 14S is supported. Transducer assembly 14S includes a transducer 14X abutting against a shoulder and facing a hollow cylindrical water-filled chamber 14C that receives water through water fitting 36. Transducer 14X is seated in a hollow cylindrical chamber backed by potting compound 51 that is seated in walls 43A and 43B of block 43 with a pair of O-rings 52 establishing a fluid tight seal that keeps water outside the region where leads 53 establish an electrical connection to transducer 14X. Shoulder screw 36' rides in slot 33' (FIG. 3).

An actual embodiment of the invention has increased the rate of tubing production from 150 feet per minute to more than 500 feet per minute while providing improved tolerances of all thickness within limits of 30/−0.00005" of a nominal wall thickness of 0.02" while maintaining the inside diameter +/−0.001" of a nominal inside diameter of 0.101" for tubing made of PVC.

There has been described novel apparatus and techniques for materially increasing the rate of production of flexible tubing while maintaining improved tolerance. It is evident that those skilled in the art may now make numerous uses and modifications of and departures from the specific apparatus and techniques described herein without departing from the inventive concepts. Consequently, the invention is to be construed as embracing each and every novel feature and novel combination of features present in or possessed by the apparatus and techniques herein disclosed and limited solely by the spirit and scope of the appended claims.

What is claimed is:

1. An ultrasonic thickness measuring system comprising,
   first and second opposed ultrasonic probes defining a channel therebetween for accommodating tubing whose thickness is to be measured thereby,
   said probes being formed with passages extending into said channel for receiving fluid under pressure for preventing bubbles in said fluid between said tubing and said probes when said tubing is in said channel,
   slotted cam means for supporting said probes and controlling their radial displacement from the axis of said channel,
   and means for rotatably supporting said cam means whereby rotation of said cam means displaces each of said probes radially by equal radial increments to maintain said probes at substantially the same radial distance from said axis.

2. An ultrasonic thickness measuring system in accordance with claim 1, and further comprising,
   third and fourth opposed ultrasonic probes adjacent to and generally orthogonal to said first and second opposed probes coacting with said first and second opposed probes to define said channel for accommodating tubing whose thickness is to be measured thereby,
   said third and fourth probes being formed with passages extending into said channel for receiving fluid under pressure for preventing bubbles in said fluid between said tubing and said probes when said tubing is in said opening,
   said slotted cam means being also for supporting said third and fourth probes and controlling their radial displacement from the axis of said channel,
   and said means for rotably supporting said cam means whereby rotation of said cam means displaces each of said probes radially by equal radial increments to maintain said probes at substantially the same radial distance from said axis.

3. An ultrasonic thickness measuring system in accordance with claims 1 or 2 and further comprising,
   a tank for holding fluid and having an input end at which said tubing enters and an output end at which said tubing exits, said probes being located in said tank in a region normally covered by said fluid, and means for delivering said fluid under pressure to said passages to keep said fluid moving between tubing when in said channel and said probes to prevent bubbles from developing between said probes and said tubing when said probes are immersed in said fluid.

4. An ultrasonic thickness measuring system in accordance with claim 3 and further comprising extrusion die means near said input end for providing extruded tubing to said tank at said input end, said probes being located in said tank much closer to said input end than to said output end, whereby the temperature of said tubing when in said channel remains substantially constant substantially at the temperature of said tubing upon exiting from said extrusion die means.

5. An ultrasonic thickness measuring system in accordance with claim 4 and further comprising, means for injecting plastic material into said extrusion die means to produce said plastic tubing at the output of said extrusion die means, means for injecting gas under pressure into said tubing to affect at least the diameter thereof, ultrasonic thickness measuring circuit means coupled to said probes for providing a signal representative of the thickness of the tubing wall when in said channel, control means responsive to said thickness signal for providing a control signal to said means for introducing gas under pressure to control the pressure of said gas and maintain the diameter of said tubing and said wall thickness substantially uniform.

6. An ultrasonic thickness measuring system in accordance with claim 5 and further comprising, means outside said tank near said output end for providing a signal representative of the diameter of said tubing, means for coupling the latter signal to said control means, and said control means being responsive to both said thickness signal and said diameter signal for providing a speed control signal, and means responsive to said speed control signal for controlling the rate at which said tubing passes through said tank to maintain said diameter and said thickness substantially uniform.

7. An ultrasonic thickness measuring system in accordance with claims 1 or 2 and further comprising, a tank for holding fluid and having an input end at which said tubing enters and an output end at which said tubing exits, said probes being located in said tank in a region normally covered by said fluid, and means for delivering said fluid under pressure to said passages to keep said fluid moving between tubing when in said channel and said probes to prevent bubbles from developing between said probes and said tubing when said probes are immersed in said fluid, said means for delivering including a source of debubbled fluid.

8. An ultrasonic thickness measuring system in accordance with claims 1 or 2 wherein each of said probes comprises an electoacoustical transducer abutting a hollow cylindrical fluid-filled chamber comprising a said passage having an opening along the axis thereof for engagement with said tubing and further comprising, means defining a water fitting extending radially through the wall of said hollow cylindrical waterfilled chamber for admitting water into the latter chamber to establish an essentially bubble-free path between said eletroacoustical transducing means and said tubing.

9. An ultrasonic thickness measuring system in accordance with claim 8 wherein said electroacoustical transducer is seated in a hollow cylindrical chamber contiguous with said hollow cylindrical water-filled chamber abutting against a shoulder at the inside end of said hollow cylindrical water-filled chamber.

10. An ultrasonic thickness measuring system in accordance with claim 1 wherein said camming means comprises an annular disk formed with at least one pair of opposed arcuate slots symmetrical about said axis spaced from said axis by a progressively changing distance as a function of angle about said axis, and water fitting means connected to each of said probes for riding in a respective one of said arcuate slots for positioning the associated probe in accordance with the angular position of said cam means about said axis and for water entry.

11. An ultrasonic thickness measuring system in accordance with claim 10 and further comprising, a pointer attached to said cam extending radially from said axis, and means defining a scale opposite said pointer for coacting therewith to provide an indication of the radial distance between each of said probes and said axis.

* * * * *